(12) United States Patent
Bishop et al.

(10) Patent No.: US 8,815,178 B2
(45) Date of Patent: Aug. 26, 2014

(54) INTEGRATED DEVICE FOR SURFACE-CONTACT SAMPLING, EXTRACTION AND ELECTROCHEMICAL MEASUREMENTS

(75) Inventors: Daniel Bishop, Phoenix, AZ (US); Jeffrey La Belle, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 163 days.

(21) Appl. No.: 13/258,585

(22) PCT Filed: Mar. 25, 2010

(86) PCT No.: PCT/US2010/028655
§ 371 (c)(1),
(2), (4) Date: Dec. 8, 2011

(87) PCT Pub. No.: WO2010/111484
PCT Pub. Date: Sep. 30, 2010

(65) Prior Publication Data
US 2012/0088258 A1    Apr. 12, 2012

Related U.S. Application Data

(60) Provisional application No. 61/163,542, filed on Mar. 26, 2009.

(51) Int. Cl.
*B01L 3/00* (2006.01)
*G01N 33/543* (2006.01)
*G01N 35/00* (2006.01)

(52) U.S. Cl.
CPC ............ *B01L 3/50273* (2013.01); *B01L 3/502* (2013.01); *B01L 3/5027* (2013.01); *B01L 3/502715* (2013.01); *B01L 2200/10* (2013.01); *B01L 2300/0816* (2013.01); *B01L 2300/0636* (2013.01); *B01L 2300/087* (2013.01); *B01L 2300/123* (2013.01); *B01L 2400/0481* (2013.01); *G01N 33/54366* (2013.01); *G01N 2035/00544* (2013.01); *G01N 2035/00128* (2013.01)
USPC ....... 422/503; 422/82.01; 422/68.1; 422/500; 422/501; 422/502; 435/4; 435/14; 435/287.3; 435/288.5; 435/286.7; 435/288.2; 435/287.1; 435/287.2; 435/288.3; 435/288.4; 436/518; 436/95; 436/149; 436/150; 436/151; 600/300; 600/318; 600/319; 600/345

(58) Field of Classification Search
CPC ................... B01L 2300/087; B01L 2300/123; B01L 2300/0636; B01L 2400/0481; B01L 2200/10; B01L 3/502; B01L 3/5027; B01L 3/502715; B01L 3/50273; G01N 33/54366; G01N 2035/00544; G01N 2035/00128
USPC .......................... 92/48–50, 89, 90, 93, 96, 97; 422/82.01; 435/4, 14; 436/95, 436/149–151; 600/318, 319, 345
See application file for complete search history.

(56) References Cited

U.S. PATENT DOCUMENTS

| | | | | |
|---|---|---|---|---|
| 6,033,628 | A * | 3/2000 | Kaltenbach et al. | 422/68.1 |
| 6,197,534 | B1 | 3/2001 | Lakowicz et al. | |
| 7,133,712 | B2 * | 11/2006 | Cohan et al. | 600/345 |
| 7,150,975 | B2 * | 12/2006 | Tamada et al. | 435/14 |
| 7,763,453 | B2 * | 7/2010 | Clemmens et al. | 435/286.7 |
| 2006/0228259 | A1 * | 10/2006 | Samsoondar | 422/82.05 |
| 2011/0113901 | A1 * | 5/2011 | Gonzalez | 73/864 |

OTHER PUBLICATIONS

Scholle et al., "Sequence of the mgIB gene from *Escherichia coli* K12: comparison of wild-type and mutant galactose chemoreceptors," Mol. Gen. Genet, 208:247-253 (1987).
Zukin et al., "Properties of the galactose binding protein of *Salmonella typhimurium* and *Escherichia coli*," Biochemistry, 16(3):381-386 (1977).
Boos et al., "Transport properties of the galactose-binding protein of *Escherichia coli*. Substrate-induced conformational change," J. Biol. Chem, 247(3):917-924 (1972).
Boos, "Structurally defective galactose-binding protein isolated from a mutant negative in the -methylgalactoside transport system of *Escherichia coli*," J. Biol. Chem., 247(17):5414-5424 (1972).

Strange et al., "Receptor interactions in a signalling system: competition between ribose receptor and galactose receptor in the chemotaxis response," Proc. Natl. Acad. Sci. USA, 73(3):762-766 (1976).

\* cited by examiner

*Primary Examiner* — Melanie Y Brown
*Assistant Examiner* — Erik B Crawford
(74) *Attorney, Agent, or Firm* — Quarles & Brady LLP; Gavin Milczarek-Desai

(57) ABSTRACT

The invention relates to a device and method for non-invasive detection of an analyte in a fluid sample. In one embodiment, the device comprises: a collection chamber containing an absorbent hydrogel material; a fluidic channel connected to the collection chamber; a sensing chamber connected to the fluidic channel, wherein the device is comprised of a compressible housing that allows transfer of fluid collected by the collection chamber to be transferred to be extracted and withdrawn to the sensing chamber upon compression of the device, wherein the sensing chamber contains a material that specifically detects the analyte and wherein the sensing chamber is operably linked to a processor containing a potentiostat that allows detection of the analyte using electrochemical sensing.

18 Claims, 13 Drawing Sheets

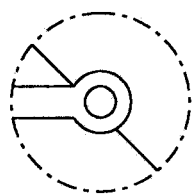
FIG. 4A-3
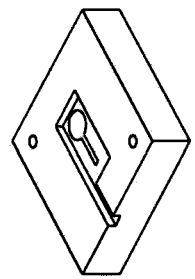
FIG. 4A-6
FIG. 4A-2
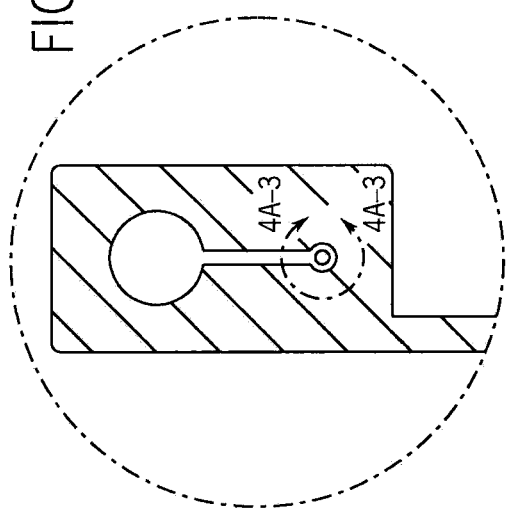
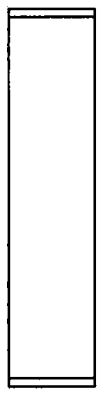
FIG. 4A-5
FIG. 4A-4
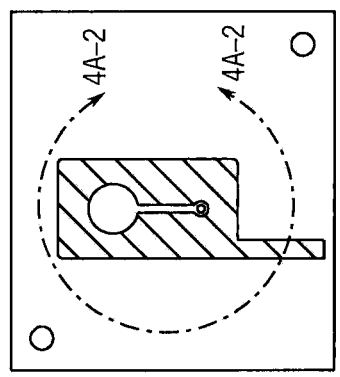
FIG. 4A-1

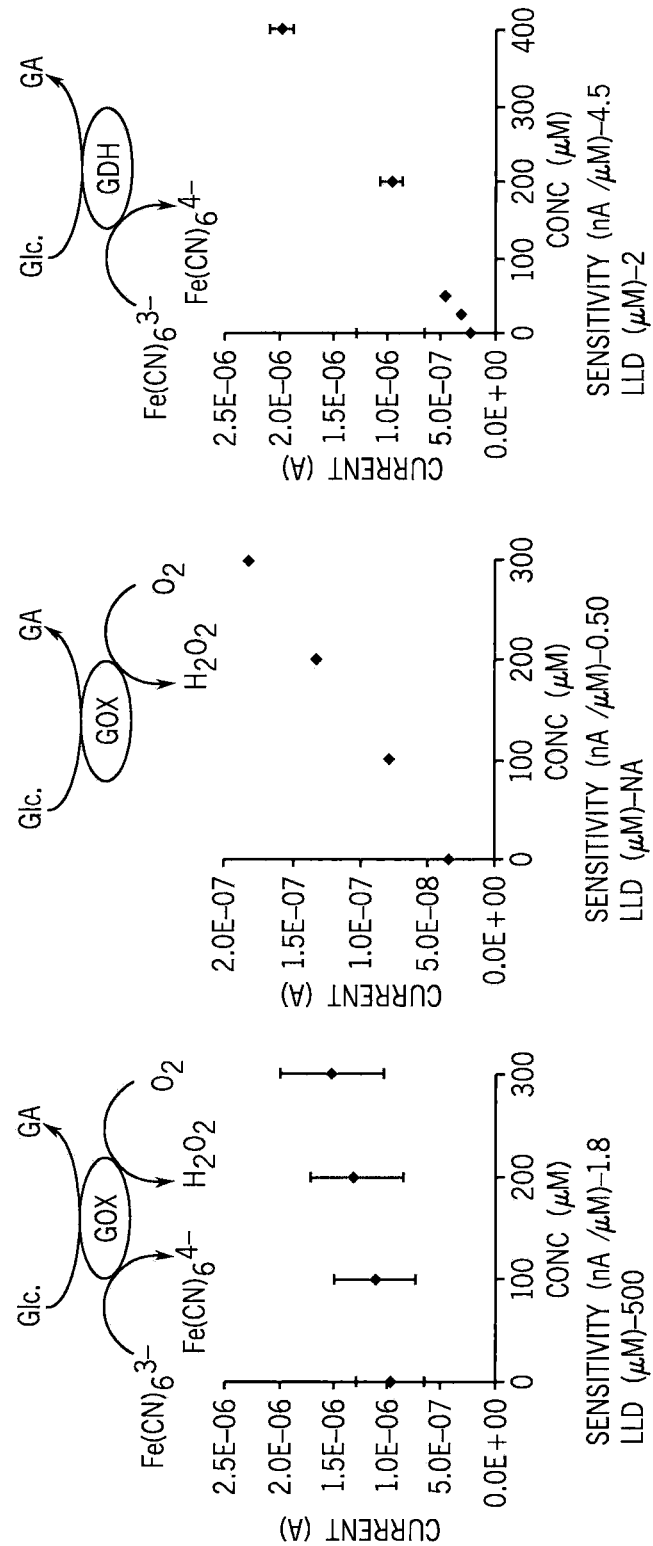

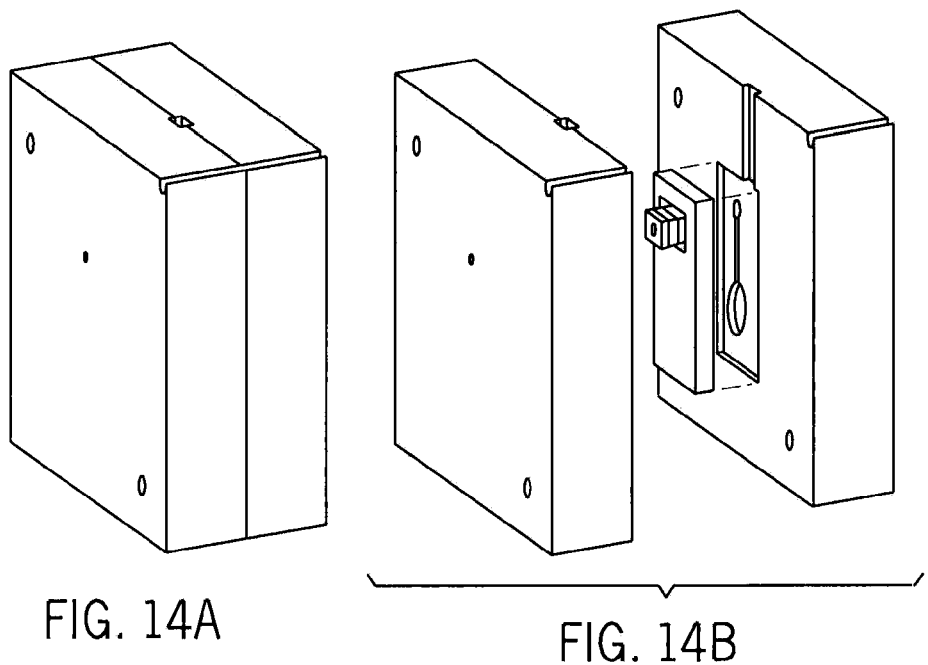
FIG. 14A
FIG. 14B
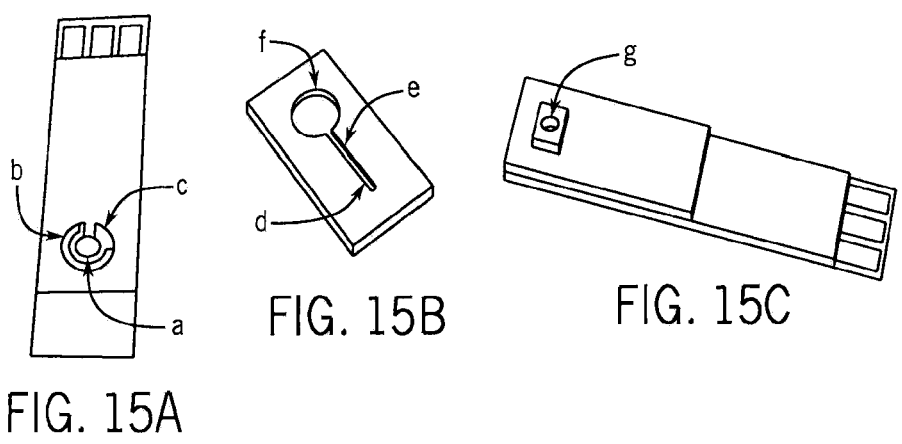
FIG. 15A
FIG. 15B
FIG. 15C

INTEGRATED DEVICE FOR SURFACE-CONTACT SAMPLING, EXTRACTION AND ELECTROCHEMICAL MEASUREMENTS

RELATED APPLICATIONS

The present application is filed pursuant to 35 U.S.C. 371 as a U.S. National Phase application of International Patent Application No. PCT/US2010/028655, which was filed Mar. 25, 2010, claiming the benefit of priority of U.S. Provisional Application No. 61/163,542, which was filed on Mar. 26, 2009. The entire text of the aforementioned applications is incorporated herein by reference.

FIELD OF THE INVENTION

The invention relates non-invasive collection and monitoring of analytes of interest from biological fluids such as tears, blood urine and the like, dry surfaces (e.g. bacterial spores from skin, trace compounds like explosives or narcotics from surface and the like.

BACKGROUND OF THE INVENTION

There is a significant need for more non-invasive monitoring of analytes in a patient. A particular disorder requiring such monitoring is diabetes mellitus, a disease that requires constant vigilance with respect to monitoring of the glucose levels of the subject. One approach to the non-invasive monitoring of blood glucose levels is to monitor glucose concentrations in tear fluid. While several methods for sensing glucose in tear fluid have been proposed, controversy remains as to the precise concentrations of tear glucose in normal and diabetic subjects and as to whether tear fluid glucose concentrations correlate with blood glucose concentrations.

The method of fluid collection has a significant impact on the level of accuracy and sensitivity of the glucose concentration measurement. Studies that involve mechanical irritation of the conjunctiva during sampling measure the highest tear glucose concentrations, while studies that avoid tear stimulation measure the lowest concentrations. Attempts to monitor tear glucose concentration in situ by using contact lens based sensing devices also are available but these contact lenses require calibration, lead to irritation after prolonged use, and are not truly "non-invasive". Overall, the prior art methods have taught various devices and have shown the importance of the sampling method in determining tear glucose concentrations.

The present invention addresses a need for a safe, fast, non-invasive, and non-irritating method and device for the collection and sampling of tears.

BRIEF SUMMARY OF THE INVENTION

The present invention relates to a device for obtaining trace fluid samples from a biological surface for electrochemical analysis and used thereof for detecting analytes in such trace fluids. The device can be used to collect tears from the surface of the eye or fluid from the surface of open wounds (e.g. ulcers). Those samples can be processed to detect metabolic products such as glucose, lactate, uric acid, ascorbic acid, catecholamines such as norepinephrine, epinephrine, and dopamine, pH, $O_2$, ions such as sodium and calcium, whole human cells, pathogens including bacteria, fungi, parasites, and viral particles, metal ions such as zinc, and protein biomarkers such as inflammatory cytokines.

Thus the invention provides a device for determining the presence of an analyte in a fluid sample comprising: a collection chamber containing an absorbent biocompatible material (e.g. fibrous networks, hydrogels, absorbent foams, sol gels, etc); a fluidic channel connect to the collection chamber; and a sensing chamber connected to the fluidic channel, wherein the device is comprised of a compressible housing that allows transfer of fluid collected by the collection chamber to be transferred to the sensing chamber upon compression of the device, wherein the sensing chamber contains a material that specifically detects the analyte and wherein the sensing chamber is operably linked to a processor containing a potentiostat that allows detection of the analyte using electrochemical sensing.

The collection chamber contains a small sample surface made of a biocompatible material such as thermoplastics such as polyethylene, polyurethane, complex thermoplastics such as styrene-ethylene/butylene-styrene (SEBS) or styrene-ethylene/propylene-styrene (SEPS), silicone rubbers (e.g. polydimethylsiloxane), hydrogels (e.g. poly(2-hydroxyethyl methacrylate)), sponges, or fibrous materials.

The sensing elements are created by standard fabrication techniques such as screen printing or other standard sensing fabrication techniques including: chemical vapor deposition, sputter deposition, and photolithography. Techniques such as injection molding, hot press, casting, and thermoforming could be used to fabricate the fluidics system. Materials such as a flexible polymer (e.g. polydimethylsiloxane) is used to fix the fluidics chamber to the surface of the sensor. The system can be filled with an extracting fluid that covers the sensing surface. The sampling feature is also attached to the fluidics system so that a channel runs between it and the sensor and fluid. By pressing on the fluidics system the fluid can be driven through the channel to the sampling feature and then retracted back to the sensing surface. The sampling feature could be pressed to a biological surface, absorbing a fixed and known amount of fluid.

The device of the invention can be placed in a processor containing a potentiostat which controls an electrode system wherein the processing of the fluid comprises applying a constant or variable voltage to the electrode system to induce an electrochemical reaction between the material that specifically detects the analyte in the fluid sample and detecting a current produced by the electrochemical reaction from the contact of the analyte with the material that specifically detects the analyte. Other standard electrochemical analytical techniques could be used that utilize constant or variable currents while monitoring voltage change, electrochemical impedance measurement, and anodic stripping voltammetry where metals ions are reduced as solid deposits on the electrode surface and then reoxidized to characterize The invention also provides a method of determining the concentration of an analyte in a fluid sample comprising receiving the fluid into the collection chamber of the device; transferring the liquid collected in step (a) to the sensing chamber of the device to determine the presence of the analyte in the fluid; and correlating the determined presence of the analyte in the liquid with a concentration of the analyte in the liquid.

In specific embodiments, the analyte is glucose.

In other specific embodiments, the fluid sample is tear fluid.

In specific aspects, the receiving the fluid in the collection chamber comprises placing the tip of the collection chamber well near the eye region of a subject. Preferably, the device receives a fluid in an amount of between about 1 µl to about 10

µl. In certain embodiments, the sensing chamber comprises glucose oxidase or glucose dehydrogenase.

In specific embodiments, the channel between the sensing chamber and the collection chamber comprises dry reagents for a glucose oxidase assay or a glucose dehydrogenase assay such that transfer of the liquid from the collection chamber through the fluid channel places all the reagents for a glucose oxidase or glucose dehydrogenase in the sensing chamber.

BRIEF DESCRIPTION OF SEVERAL VIEWS OF THE DRAWINGS

FIGS. 4A-4B show the specifications for molding a device of the invention.

FIGS. 11A-11C show diagrams of the enzymatic reaction and sensor performance including sensitivity and estimated lower limit of detection (LLD) for (FIG. 11A) GOX/Ferricyanide, (FIG. 11B) GOX/$O_2$/PB, and (FIG. 11C) GDH/Ferricyanide. Chronoamperometric measurements were carried out at +0.45 V, −0.1 V, and +0.45 V vs. the silver pseudoreference 10 sec after applying the potential. Error bars represent one standard deviation.

FIGS. 14A-14B show CAD schematic of the mold assembly showing both halves of the mold (FIG. 14A) and CAD of the actual part fabricated (FIG. 14B).

FIG. 15A Screen print electrode with (a) working, (b) counter, and (c) reference electrodes. In FIGS. 15B-15C the microfluidic capture system can be seen with the sample inlet (d), channel (e), and sensing well (f) that also acts as the pump. In (c) the inset (g) that is used to hold the biocompatible capture material is shown.

DETAILED DESCRIPTION OF THE INVENTION

Figure 1A:
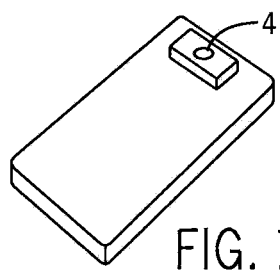
FIGS. 1A-1D show a prototype design of the present invention inside a casing.
Figure 1B:
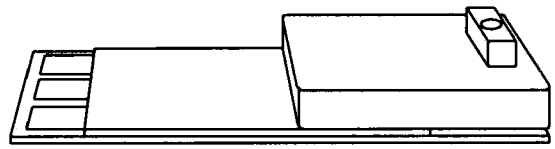
Figure 1C:
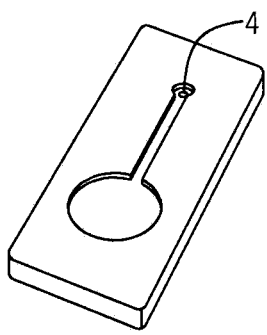
Figure 1D:
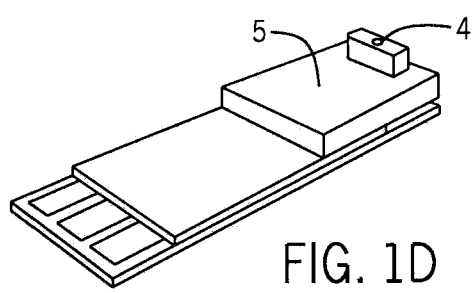

The present invention provides a device for obtaining trace fluid samples from a biological surface for electrochemical analysis. The device contains a sampling feature into which the sample is collected. The sampling feature has a small sample surface made of a biocompatible material thermoplastics such as polyethylene, polyurethane, complex thermoplastics such as styrene-ethylene/butylene-styrene (SEBS) or styrene-ethylene/propylene-styrene (SEPS), polyethylene, polyurethane, silicone rubbers (e.g. polydimethylsiloxane), hydrogels (e.g. poly(2-hydroxyethyl methacrylate)), sponges (e.g. polyurethane foams), or fibrous materials. There is also an electrochemical sensor created by standard fabrication techniques (e.g. screen printing). A fluidics system made of a flexible polymer (e.g. polydimethylsiloxane) is fixed to the surface of the sensor. The system can be filled with a fluid that covers the sensing surface. The sampling feature is also attached to the fluidics system so that a channel runs between it and the sensor and fluid.

By pressing on the fluidics system the fluid can be driven through the channel to the sampling feature and then retracted back to the sensing surface. The sampling feature could be pressed to a biological surface, absorbing a known amount of fluid. Using the fluidics system, the sensor fluid could be driven up to extract the sample fluid from the sampling feature and then allowed to flow back over the sensing surface for electrochemical analysis. This device could be made to be reusable or disposable. In one application example, the device can be used to measure glucose concentrations from tear fluid on the surface of the eye. Glucose assay reagents including an enzyme (e.g. glucose oxidase or glucose dehydrogenase) and mediator (e.g. ferrocene or potassium ferricyanide) could be included in the fluid of the system or applied in dry form to the channel for mixing during sample extraction.

This device could be used by diabetics as a replacement for current needle-based sampling systems or as a supplemental measurement to improve glycemic control between needle-based measurements. Such a sensor would need to reproducibly capture tear fluid volumes on the order of single 1's to 10's µL to measure glucose in the physiologically relevant range of 1's to 100's µM using enzyme-based electrochemical techniques such as amperometry, chronoamperometry, and coulometry. Since tear glucose concentrations are particularly low, techniques to enhance sensitivity could be employed such as applying electrical overpotentials to the sensor prior to sampling glucose. Alternately, reagents could be added to the assay for chemical or enzymatic neutralization of biological compounds that interfere with electrochemical measurements. An example of this approach would be to include uricase to enzymatically oxidize uric acid into products that no longer interfere with glucose measurements.

In addition to detecting glucose, other analytes also could be tested by the device described herein. Such other metabolites include markers of oxygen consumption, stress, injury, and other physiological parameters including but not limited to lactate, norepinpherine, urea, ion concentrations, pH, and oxygen. Proteins and other biomarkers for detection and diagnosis of disease and other health states including but not limited to inflammatory cytokine proteins and antibody expression can also be monitored by the present invention. Biological fluids may be from any source including epithelial surface sampling sites for medical assessment including but not limited to infections, ulcers, lacerations, burns, and oral cavities, sweat, urine, blood, and saliva. In some embodiments, the biological fluid tested could be a surgically accessible fluid from the surfaces of internal tissue and organs for analysis and medical treatment including but not limited to hormone excretions from glands, neurotransmitters from nerves and tissues, and various cancerous tissue.

The device also may be used to monitor of analytes from alternate biological sources including but not limited to cell cultures, animal samples, and bioreactors or to monitor environmental analytes including but not limited to pollution particulate sampling and fluid sampling.

In addition, the present invention could be used in a variety of other fields. For example, in environmental and security testing, many compounds of interest are not water-soluble. The fluidics system could potentially be filled with alternate solvents that would allow the device to swab for explosives or chemical contaminants. In security applications the device of the invention may be used for the detection of dangerous agents including but not limited to explosives, chemical agents, and biological agents from various dry surfaces such as luggage and packages and biological surfaces such as skin. In forensic science applications, the device could be used to sample forensic biological materials including but not limited to blood, skin, hair, and other fluids.

The present invention provides a sensing system and method of extraction of tear fluid/analytes. The system combines a first chamber that comprises a sampling surface made of a material e.g., a 'capture polymer' that absorbs the fluid to be tested linked through a fluidics channel to a sensor chamber as shown in FIGS. 1A-1D and 2. While the examples described herein focus on collection and sensing of tear-glucose concentration, it should be understood that the system may readily be employed for sensing of other tear-analytes, and could be extended for analysis of samples from open-wounds or other moist biological surfaces.

Figure 2:
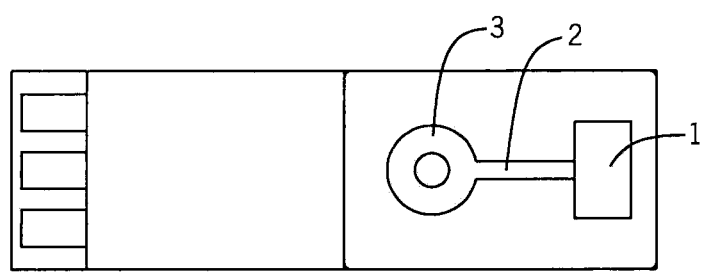
FIG. 2 shows a prototype of the present invention having a fluid collection chamber (1), sensing chamber (3) linked to the fluid collection chamber through a fluid channel (2).

Referring to FIGS. 1A-1D, the invention involves an integrated fluidics system that contains a sample collection well connected to sensor for detection. The integrated fluidic design is made of a single silicon piece that can store fluid. A prototype design is shown in FIG. 2.

The fluid chamber (1) preferably contains a biocompatible, absorbent material that is able to absorb the biological fluid. Once the gel has absorbed the fluid, the collected fluid can be transported to the sensor chamber (3) through a channel (2). The fluid chamber (1) provides the function of holding the biocompatible, absorbent material and makes for an easy interface between the device and the sampling surface. The channel (2) provides for a direct fluidic linkage between the fluid chamber (1) and the sensing chamber (3) as well as can contain dry regents. The sensor chamber (3) provides the function of acting as a reservoir, a mechanical pump, and the sensing well. The device is formed such that simple mechanical compression of the device at the sensing chamber (3) causes the extraction fluid in the sensing chamber to be driven through a channel (2) to the well opening (1), dissolving the absorbed fluid sample. Releasing the mechanical compression will then cause the extraction fluid and sample to be withdrawn back into the sensing chamber. Sample collection involves placing the device with the well opening 4 in contact with a surface, capturing a sample into the absorbent material.

The hydrogel component in the device is placed in the well in a substantially dry state and preferably has a uniform cross-section. It thus serves as a wick to absorb the tear fluid. The "hydrogel material" preferably is a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "monomer" is a low molecular weight compound that can be polymerized whereas a "macromer" refers to a medium and high molecular weight compound or polymer that contains functional groups capable of further polymerization. Medium and high molecular weight typically means average molecular weights greater than 700 Daltons.

A "hydrophilic vinylic monomer" refers to a monomer which as a homopolymer typically yields a polymer that is water-soluble or can absorb at least 10 percent by weight water. Suitable hydrophilic vinylic comonomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino- (whereby the term "amino" also includes quaternary ammonium), mono-lower-alkylamino- or di-lower-alkylamino-lower-alkyl-acrylates and -methacrylates, allyl alcohol and the like. Preference is given e.g. to hydroxy-substituted C2-C4-alkyl(meth)acrylates, five- to seven-membered N-vinyl-lactams, N,N-di-C1-C4-alkyl-methacrylamides and vinylically unsaturated carboxylic acids with a total of 3 to 5 carbon atoms. Examples of suitable hydrophilic vinylic comonomers include hydroxyethyl methacrylate, hydroxyethyl acrylate, acrylamide, methacrylamide, dimethylacrylamide, allyl alcohol, vinyl pyridine, vinyl pyrrolidone, glycerol methacrylate, N-(1,1-dimethyl-3-oxobutyl)acrylamide, and the like.

Any known, suitable hydrogels can be used in the invention. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, thermoplastics such as polyethylene, polyurethane, complex thermoplastics such as styrene-ethylene/butylene-styrene (SEBS) or styrene-ethylene/propylene-styrene (SEPS), silicone-containing hydrogels, polyurethane, polyurea, and the like. A hydrogel can be prepared according to any methods known to a person skilled in the art and placed in the collection well of the devices of the present invention.

In operation, the device is contacted with a solution that contains the analyte of interest, e.g., tears from the surface of the eye or fluid from the surface of open wounds (e.g. ulcers) and swells to absorb the solution containing the analyte of interest. The term "analyte" refers to a substance being tested. Examples of measurable analytes to be measured by the device of the invention include metabolites such as glucose, lactate, uric acid, ascorbic acid, catecholamines such as norepinephrine, epinephrine, and dopamine, pH, $O_2$, ions such as sodium and calcium, whole human cells, pathogens including bacteria, fungi, parasites, and viral particles, metal ions such as zinc, and protein biomarkers such as inflammatory cytokines. Exemplary analytes of interest include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone, obesity hormones such as leptin, serotonin and the like), chronically administered medications (e.g., dilantin, phenobarbital, propranolol), acutely administered medications (e.g., cocaine, heroin, ketamine), small molecule hormones (e.g., thyroid hormones, ACTH, estrogen, cortisol, estrogen, and other metabolic steroids), markers of inflammation and/or allergy (e.g., histamine, IgE, cytokines), lipids (e.g., cholesterol), proteins and enzymes (e.g., lactoferrin, lysozymes, tear-specific prealbumin, albumin, complement, coagulation factors, liver function enzymes, heart damage enzymes, ferritin), markers of infection (e.g., virus components, immunoglobulins such as IgM, IgG, etc., proteases, protease inhibitors), whole cells, and/or metabolites (e.g., lactate, ketone bodies).

The analyte of interest can be assayed directly in the device of the invention as the analyte flows through the channel (2) and comes into contact with the reagents used for assaying the analyte of interest which are disposed in the sensing chamber (3).

Assaying of the analyte will be carried out with the help of a testing agent composition which specifically reacts or interacts with the analyte of interest, leading to formation of a detectable signal. A detectable signal, for example, can be electrical signals (electrochemical assays), or optical signals (enzyme assays, immunoassays or competitive binding assays). Exemplary electrical signals are electrical potentials, electrical impedance, and currents. Optical signals refers to changes in the optical properties, including, but not limited to, a color formation, a change in color, fluorescence, luminescence, chemiluminescence, changes in fluorescence or luminescence intensity, changes in fluorescence or luminescence lifetimes, fluorescent anisotropy or polarization, a spectral shift of the emission spectrum, time-resolved anisotropy decay, and the like.

Electrochemical assay of the analyte of interest is largely carried out by using an enzymatic electrode (or biosensor) which consists of a thin layer of enzymes adsorbed to the active surface of a transducer or dissolved in the assay solution. Along with a suitable reference electrode and a circuit, a biosensor allows to measure either the potential difference generated between the two electrodes (for potentiometric measurements), the electrochemical impedance between the two electrodes (impedimetric measurements), or the current that flows between the two electrodes (for amperometric measurements). An example of a biosensor is a glucose biosensor, which consists of a carbon electrode with a conductive coating containing a mixture of glucose oxidase and mediator. At the working electrode surface glucose is oxidized by the glucose oxidase enzyme. This reaction causes the mediator to be reduced. At the fixed potential, applied between the two electrodes the mediator is oxidized, generating a signal response which correlates with the glucose concentration in a sample.

The tear fluid is collected in the collection well and absorbed into the hydrogel. The tear fluid is then brought into contact with an enzyme electrode and a reference electrode, by compressing the hydrogel to release the fluid contained therein. When the fluid flows through the channel and comes into contact with the sensing chamber, a potential is applied between the two electrodes to obtain an amperometric signal (current) that correlates with the concentration of the analyte of interest.

Immunoassay has been widely used in the determination of an analyte of interest in a biological fluid, such as urine or serum. For example, lactoferrin can be assayed by a solid phase ELISA test similar to that for LactoCards test. In another example, glucose can be assayed based on the Trinder reaction. Typically in the Trinder reaction, glucose oxidase, in the presence of oxygen, oxidizes glucose to form gluconic acid and hydrogen peroxide which in turn reacts with a chromogenic oxidation/reduction indicator (e.g., phenol, 3-hydroxy-2,4,6-triiodobenzoic acid, 3-hydroxy-2,4,6-tribromobenzoic acid, etc.) in the presence of peroxidase to form a color different from its original color or to generate a chemiluminescence. The Trinder reaction can be used to determine other analytes of interest so long as an analyte-specific oxidase can be obtained and used.

Binding assays and competitive binding assays have been widely used in the determination of an analyte of interest in a sample. Typically, a binding assay (without use of any competitor) is generally carried out by using a protein or fragment thereof or a chemical compound (as a receptor) that is capable of binding said analyte (ligand) in said sample and has a detectable optical signal (or other detectable signal) that changes in a concentration-dependent manner when the protein is bound to said analyte. A competitive binding assay is based on the competition between a labeled ligand (analyte) or ligand analogue (analyte-analogue) and an unlabeled ligand (analyte) in the reaction with a receptor (e.g., antibody, receptor, transport protein, chemical compound).

The detectable optical signal results from one or more labels associated with a receptor and/or a competitor. A label may be covalently or non-covalently bound to a receptor or a competitor. A "receptor" refers to a protein or fragment thereof or a chemical compound that is capable of binding reversibly an analyte of interest in a sample. A "competitor" refers to a molecule or moiety that competes with an analyte of interest for binding to a receptor.

A wide range of suitable labels are known. For example, the label may be a fluorescent label. "A fluorescent label" refers to a moiety that comprises at least one fluorophore and that, when attached to a molecule, render such molecule detectable using fluorescent detection means. Exemplary fluorophores include xanthene-type dyes, fluorescein-type dyes, rhodamine-type dyes, cyanine-type dyes, and the like. A fluorophore can also be a fluorescent protein such as phycobiliproteins or nanoparticles such as quantum dots.

The detectable optical signal can be derived from a pair of fluorophores, a first fluorophore and a second fluorophore, performing fluorescence resonance energy transfer. One of the two fluorophores can be an energy donor, for example the first fluorophore, which absorbs energy upon excitation at an excitation wavelength within its absorption spectrum and emits energy at a wavelength within its emission spectrum, and the other fluorophore can be an energy acceptor, for example the second fluorophore, which accepts the energy emitted by the donor at a wavelength within the absorption spectrum of the acceptor and emits energy at a wavelength within the emission spectrum of the acceptor. The wavelength of the absorption maximum of the donor fluorophore is shorter than the wavelength of the absorption maximum of the acceptor fluorophore; and the wavelength of the emission maximum of the donor fluorophore is shorter than the wavelength of the emission maximum of the acceptor fluorophore. It is known that the energy transfer efficiency depends on the several factors such as spectral overlap between the emission spectrum of the donor and the absorption spectrum of the acceptor, spatial distance between donor and acceptor fluorophores, relative orientation of donor and acceptor fluorophore, quantum yield of the donor and excited state lifetime of the donor. It is well known to a person skilled in the art how to select a donor fluorophore and an acceptor fluorophore. In a binding assay system, the energy donor fluorophore and the energy acceptor fluorophore each can be bound to a receptor and spaced such that there is a detectable optical signal when the receptor is bound to the analyte. In a competitive binding assay system, one of the energy donor fluorophore and the energy acceptor fluorophore can be bound to the receptor and the other can be bound to the competitor. The person skilled in the art will understand that any type of optical detection method may be used including detection methods that rely on quenching or inhibition of a signal. FRET based detection methods may be used.

It is understood that the above energy acceptor fluorophore can be replaced by a non-fluorescent energy transfer acceptor, for example, such as a dye which accepts the energy emitted by the donor fluorophore at a wavelength within the absorption spectrum of the acceptor but does not emits energy in the form of fluorescence or luminescence.

A fluorescent label can intrinsically be part of the receptor. For example, a receptor can be a fusion protein comprising at least the fluorescent part of a fluorescent protein and at least the binding part of a receptor protein. Alternatively, the fluorescent label can be a fluorescent label which is not naturally associated with the receptor moiety but which is attached by means of a chemical linkage, such as a covalent bond.

A fluorescent label can intrinsically be part of the competitor. Alternatively, the fluorescent label can be a fluorescent label which is not naturally associated with the competitor moiety but which is attached by means of a chemical linkage, such as a covalent bond.

One example of binding assay is an assay for glucose disclosed in U.S. Pat. No. 6,197,534, using an E. coli glucose/galactose binding protein ("GGBP") as previously described (Scholle, et al., Mol. Gen. Genet. 208:247-253 (1987)), or functionally equivalent fragments thereof. As a sensor for glucose monitoring, GGBP has several favorable features including a single glucose binding site and high affinity for glucose; GGBP binds glucose with a dissociation constant near 0.8 µM. Like similar transport proteins from other bacteria, GGBP is highly specific for binding glucose and/or galactose. The apparent binding affinity of GGBP for sugars other than glucose or galactose is typically 100-1000 fold weaker [Boos, et al., J. Biol. Chem. 247(3):917-924 (1972); Boos, W., J. Biol. Chem. 247(17):5414-5424 (1972); Strange and Koshland, Proc. Nat'l Acad. Sci. USA 73(3):762-766 (1976); Zukin, et al., Biochemistry 16(3):381-386 (1977)). The high affinity for glucose also will allow to measure µM glucose concentrations in a tear fluid. GGBP can be labeled with one fluorescence energy donner moiety and one fluorescence energy acceptor at two specific position on GGBP in a manner so that there is a detectable spectral change (e.g., change in fluorescence intensity or lifetime) when GGBP is bound to glucose.

The device offers a minimally-invasive method for obtaining/analyzing fluids from a biological surface. Thus, more invasive sampling/measurement methods (e.g. needle-based or implantables) can be avoided. Also, a touch surface is ideal for contacting sensitive areas of the body such as the eyes or open wounds. Specific to glucose in tears, a number of studies have investigated the topic without reaching consensus on many issues. The technical challenges of careful sampling of micro-liter volumes of tear fluid and then extracting and measuring the fluid have been largely addressed through current research in the lab (see research progress in attached powerpoint) which has resulted in a physical prototype.

EXAMPLE 1

Initial Design

Figure 3A:
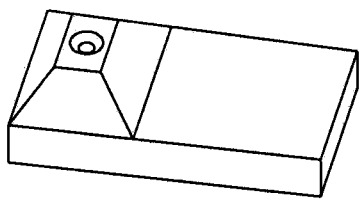
FIGS. 3A-3B show two aspects of the prototype.
Figure 3B:
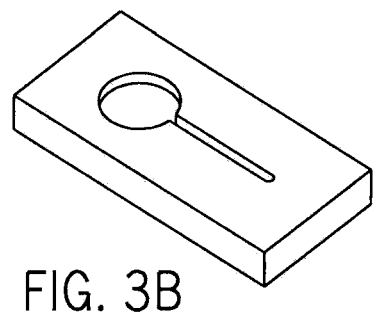

FIG. 3A and FIG. 3B show the design of the new integrated fluidics design for sampling and testing tear analytes. It consists of a single silicone piece which is fixed to a screen print's surface. It has the advantage that the single silicone piece can store fluid that is collected in the raised sampling portion. Compressing that raised sampling portion pushes the fluid up to sampling film for extraction. Once the compression is released, the liquid is drawn back to sensor for detection Dry reagents could conceivably be stored in channel for long term storage.

Extracting fluids could conceivably be contained using a simple fluidics valve which allows said fluid to be contained with decreased evaporation until time of use.

Figures 3, 4B:
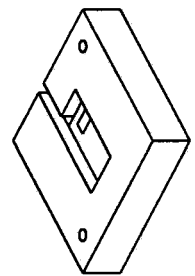

The device was designed using the molding shown in FIG. 4A and FIG. 4B.

Figure 5A:
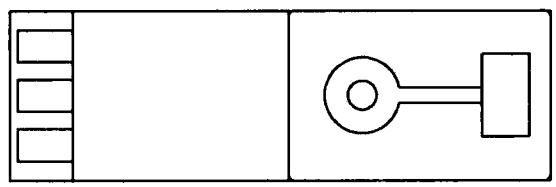
FIGS. 5A-5F show operation of a device of the invention using Rhodamine 6 G.
Figure 5B:
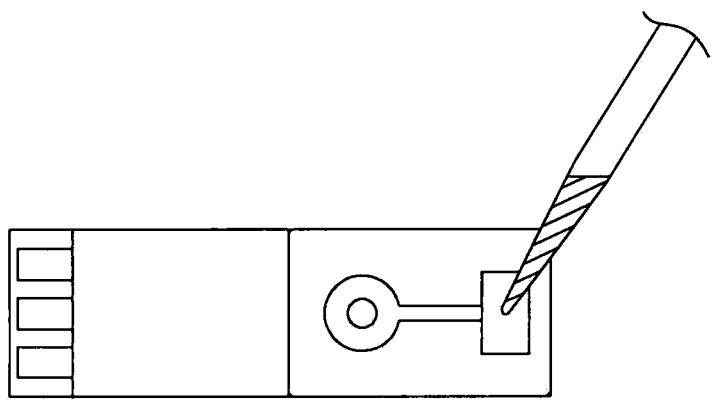
Figure 5C:
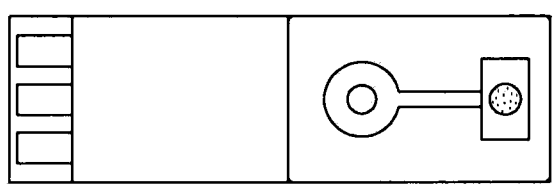
Figure 5D:
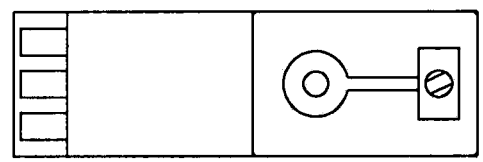
Figure 5E:
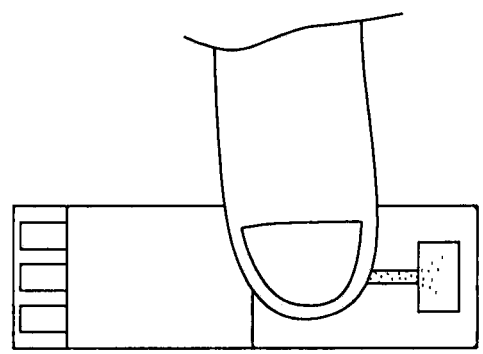
Figure 5F:
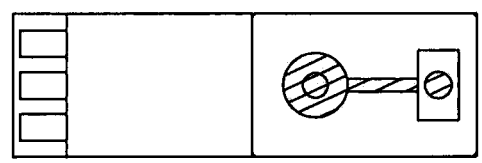
Figure 6:
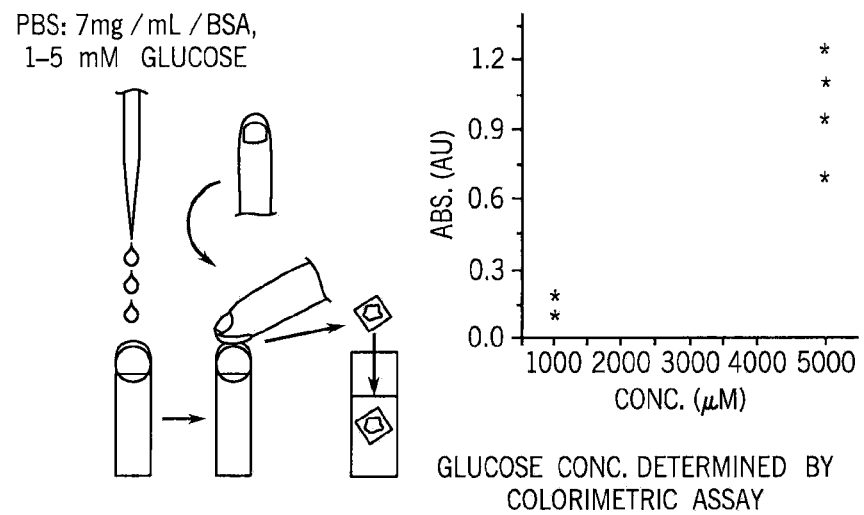
FIG. 6 shows glucose capture data on calcium alginate as a capture medium.

The operation of the device is shown by reference to the prototype produced in clear plastic and shown in FIGS. 5A-5F. In this FIG. 5A there is shown the prototype. FIG. 5B shows delivering of 1 µl of rhodamine 6G into the capture hydrogel which is part of the sampling section. FIG. 5C shows absorption of the fluid into the hydrogel as can be seen more clearly under UV illumination depicted in FIG. 5D. Compression of the device (shown in FIG. 5E) allows the liquid absorbed onto the hydrogel to transfer to the sensing chamber as shown in FIG. 5F.

Figures 4, 4B, 5, 6:
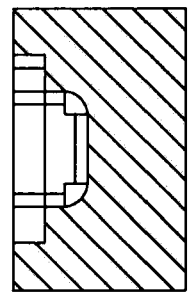
Figures 2, 4B:
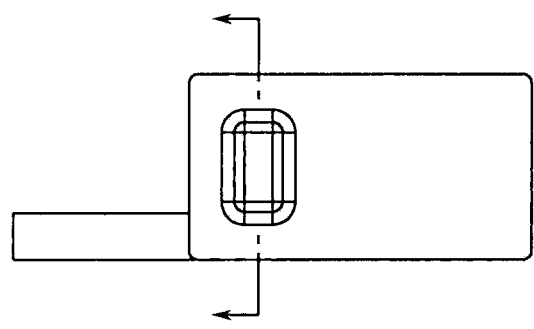
Figures 4, 4B, 5:
Figures 1, 4B:
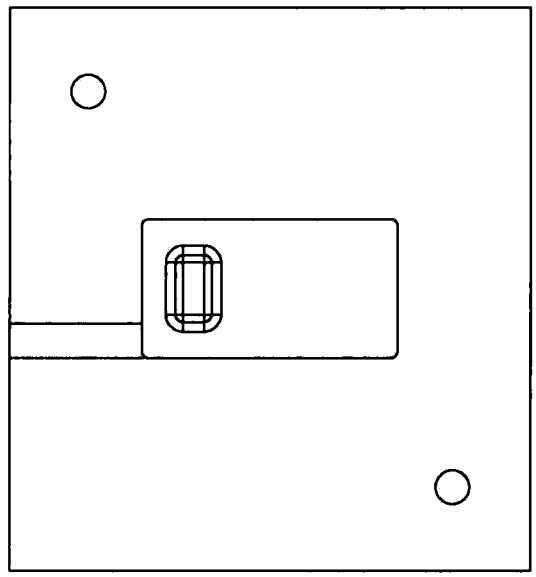
Figures 4, 4B:

As noted above, the hydrogel component used for the capture of the analyte into the device may be any hydrogel. In an exemplary embodiment, calcium alginate was used as a possible sampling material. Using calcium alginate the inventors demonstrated that the device shown in e.g., FIGS. 5A-5F had the ability to sample and release glucose from an eye-like surface. (see FIG. 6 for data on calcium alginate as a capture medium). Calcium alginate offers a number of advantages in that it is a simple crosslinking, biocompatible, possibility of chemically initiated dissolution with $Ca^{2+}$ binding agents. However, it has relatively slow absorption of fluids, significant shrinkage during crosslinking, poor reuse after hydrogel completely dries out. As such, an alternative embodiment employs poly 2-hydroxyethyl methacrylate (pHEMA) as a capture hydrogel. The preferred material is a polyurethane foam.

Figure 7:
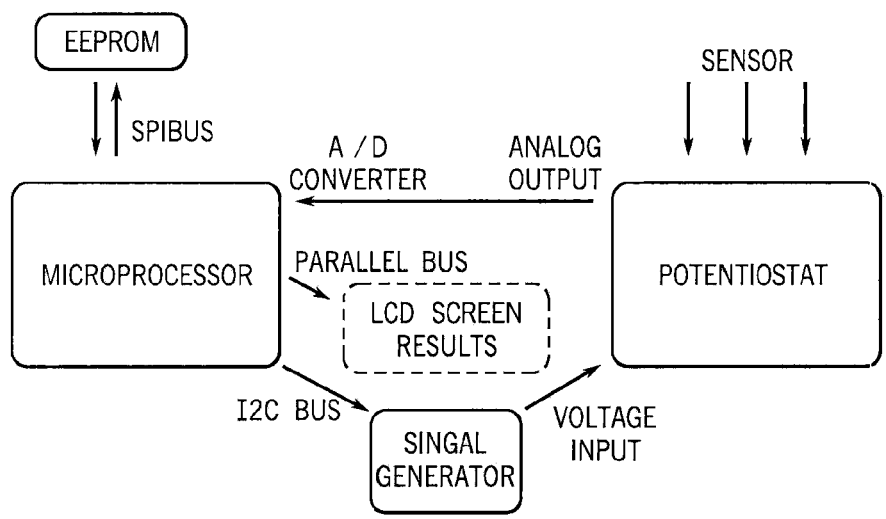
FIG. 7 shows an example of a hand-held apparatus designed to monitor analyte concentration from a device of the invention.
Figure 8:
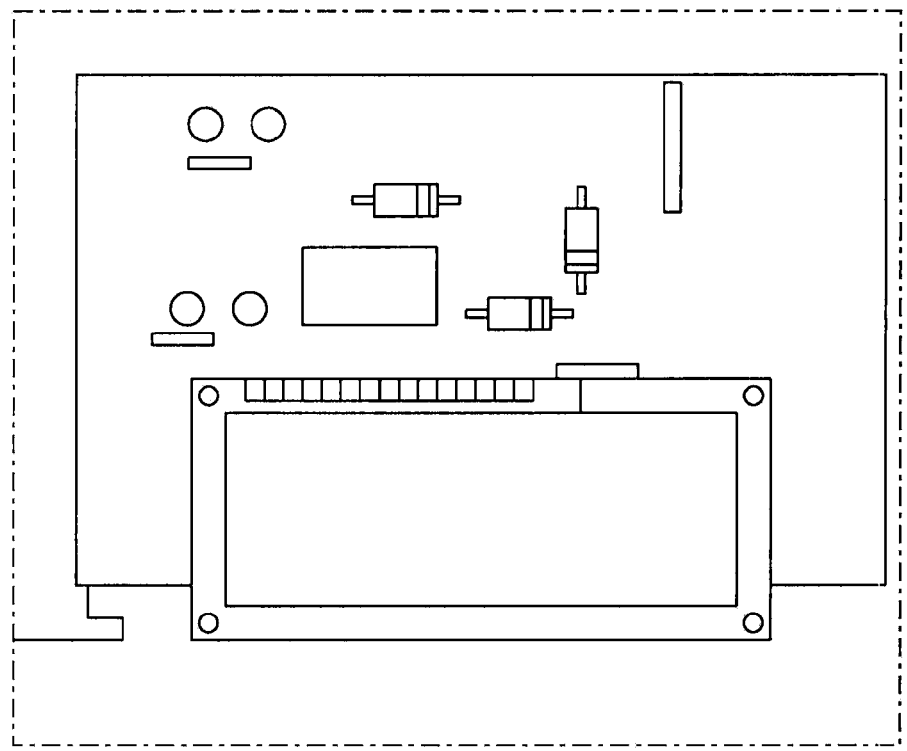
FIG. 8 shows a prototype of the design of claim 7.

The sensor portion of the device is connected to instrumentation that allows quantification of the signal to assess the amount of glucose in the sampled fluid. FIG. 7 shows an example of a hand-held apparatus designed for this purpose and a prototype of this design is shown in FIG. 8.

Table 1 shows data from initial testing of the integrated sensors described herein. 6 sensors were tested. The sensors had a pHEMA saturated sheet in the collection chamber which was saturated with 1 mM Ferrocyanide (co-product of enzymatic reaction).

| Sensor | Pre-weight (g) | Post-weight (g) | Volume (uL) | Injection Time (s) |
|---|---|---|---|---|
| 1 | 1.4465 | 1.4754 | 28.9 | 100 |
| 2 | 1.4683 | 1.4973 | 29 | 100 |
| 3 | 1.4656 | 1.4956 | 30 | 100 |

| Sensor | Pre-weight (g) | Post-weight (g) | Volume (uL) | Injection Time (s) |
|---|---|---|---|---|
| 4 | 1.471 | 1.5011 | 30.1 | 100 |
| | | MEAN VOL | 29.5 | |
| | | STD DEV | 0.64 | |
| | | RSD | 2.16% | |

Figure 9:
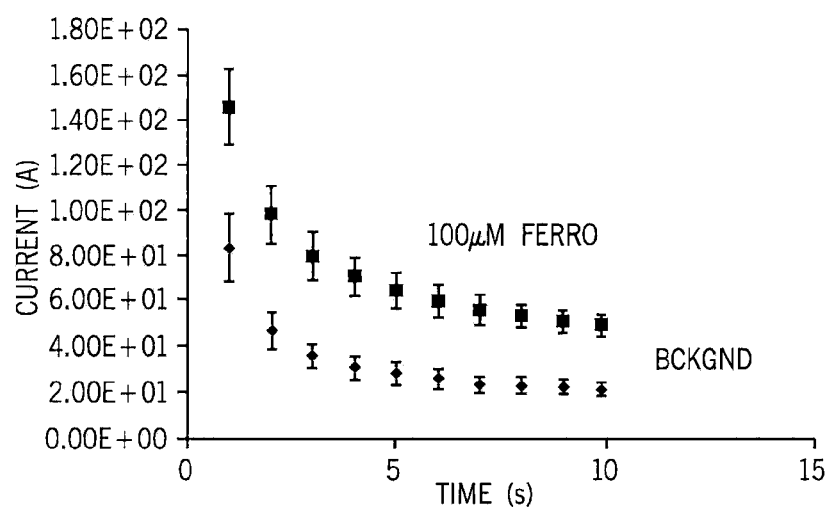
FIG. 9 shows the data from a glucose detection assay performed using the devices of the invention over a range of 0 to 100 uM glucose.

FIG. 9 shows the data from a glucose detection assay performed using the devices of the invention over a range of 0 to 100 µM glucose. These values have previously been identified as the lowest necessary resolution that needs to be demonstrated for a working sample. The data showed an upward trend (n=5), but the detection was noisy and lead to the decision to reduce the final sample volume to improve the dilution factor.

The inventors reduced the mold volume of the collection well from ~30 uL to ~11 uL. The experiment was then repeated but 4 sensors failed during fabrication due to poor adhesive and injection problems. However, the remaining sensors showed definitive resolution between 0 and 100 µM, the minimal resolution between hypoglycemic and normal blood sugar. For future assembly to improve fabrication, PDMS was identified as a better adhesive for future assembly.

EXAMPLE 2

Design and Concept Testing of Disposable Tear Glucose Biosensor

As discussed herein above, monitoring tear glucose levels has potential as an approach for the non-invasive estimation of blood glucose. The present Example provides details of the production of a device that meets the needs of a tear glucose biosensor.

To briefly summarize the present example, three approaches for chronoamperometric glucose sensing were evaluated including glucose oxidase mediated by potassium ferricyanide or oxygen with hydrogen peroxide catalyst, Prussian Blue, and potassium ferricyanide mediated glucose dehydrogenase. For tear sampling, calcium alginate, poly(2-hydroxyethyl methacrylate), and polyurethane foam were screened as an absorbent tear sampling material. A quantitative model based on the proposed function of concept device was created.

For glucose sensing, it was found that potassium ferricyanide with glucose dehydrogenase was ideal, featuring oxygen insensitivity, long-term stability, and a lower limit of detection of 2 µM glucose. Polyurethane foam possessed all of the required characteristics for tear sampling including reproducible sampling from a hydrogel, simulated, eye surface (4.2±0.5 µL; n=8). It is estimated that a 100 µM glucose tear fluid would yield 135 nA (14.9% relative standard deviation).

The design needs identified for a tear sampling device are shown in (Table 2). These design needs address issues of concept functionality and usability which must be achieved before transitioning to more rigorous formal device evaluation by accepted "standards" criteria for FDA approved SMBG technologies. It was determined that a modified approach to a "mechanical" sampling approach offered an excellent balance of capabilities and drawbacks. Specifically, the use of absorbent materials in direct contact with the eye allows rapid and simple sampling. Such material could be selected from soft polyurethane (PU) foams or absorbent hydrogels which are widely used in the medical field. For glucose detection, electrochemistry offers many of the advantages found in current SMBG test strips such as sensitivity, rapidity, reproducibility, and simplicity of instrumentation. The current prevalence of electrochemical systems on the market for SMBG provides a substantial body of research in the design and optimization of electrochemical glucose sensor on which to build.

TABLE 2

| Design Need |
|---|
| reproducibly sample from tear film |
| accurately analyze glucose concentrations (1 to 1000 uM) |
| capture adequate fluid for analysis technique |
| minimal tear sampling time |
| simple tear sampling |
| simple glucose analysis |
| integrated sampling and sensing |
| low cost and scalable fabrication |

Assuming an absorbent material will be implemented for sampling tears, one immediate challenge is the integration of such a system to an electrochemical sensor. Typically, SMBG test strips have adequate fluid to both dissolve electrochemical assay components as well as create a conductive solution for electrochemical measurements. This presents a distinct challenge for an absorbent strip type system as it is unlikely that adequate tears can be collected to hydrate an assay and it is not readily apparent how to extract absorbed tears for analysis.

Figure 10A:
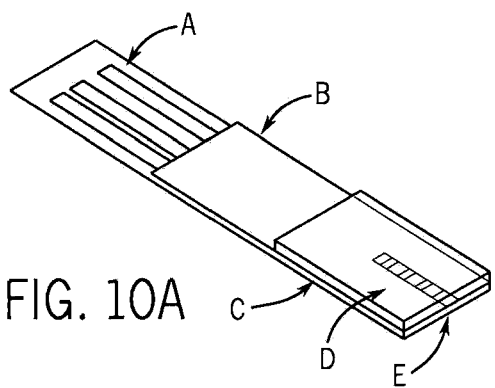
FIGS. 10A-10B show an integrated device of the invention for sampling and sensing of tear glucose. Features (A) screen printed electrical leads, (B) an insulating layer, (C) a silicone fluidics piece, (D) a sensing well covering the 3 electrode system, and (E) an absorbent sampling material.
Figure 10B:
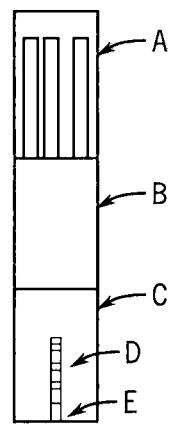

To integrate these components, a small microfluidics system is used. This fluidics system features a sensing chamber connected by a channel to an external sampling feature in which an absorbent material is placed (FIGS. 10A-10B). By pre-filling this chamber with solution, the well can be mechanically compressed, driving the fluid to the absorbent material. Upon releasing the compression, the extracted tear sample is drawn back into the sensing chamber for analysis, also dissolving any dry reagents for detection. This new concept offers an approach to the sampling and electrochemical analysis of TG that addresses the needs identified above.

The following description presents the initial results from glucose sensing, fluid sampling, sample extraction, and microfluidic design—the primary functions of the device. A quantitative model is also presented which is used to estimate final device feasibility based on initial results. These results indicate that a low-cost, sensitive, easy-to-use, TG device is achievable and within reach of current technical capabilities.

Materials/Methods

Model Development

Before initiating any actual experiments, the presented concept was translated into a series of systematic steps which could be mathematically modeled to predict system outputs and error propagation. Using standard spreadsheet software (Microsoft Excel 2007, Microsoft Corporation, Richmond, Va., USA) the equations were organized sequentially by the order each modeled step would be performed in the operation of the device. Thus, the output of each step (i.e. glucose concentration, sensor current) and their corresponding variation could be followed through entire device operation for the input parameters determined during initial bench testing.

Chemicals

All reagents were obtained from Sigma-Aldrich unless otherwise specified. Glucose dehydrogenase with flavin adenine dinucleotide cofactor (GDH-FAD) with an activity of 207 U/mg was generously donated by Amano Inc. (Japan). The glucose oxidase (GOx) used had an activity of 155.6

U/mg. All solutions were prepared in phosphate buffered saline (PBS) at pH 7.4 unless otherwise specified Electrochemical Detection For electrochemical glucose sensing, a disposable, commercial screen-print sensor (Zensor, Taiwan) was selected. The sensor featured a working (71.0 mm$^2$) and counter electrode made of conductive carbon ink, a pseudoreference electrode made of silver ink (−72 mV vs Ag/AgCl), and a non-conducting insulating layer. A CHI 1230A potentiostat (CHI, Austin, Tex., USA) connected to a desktop computer was used to make electrochemical measurements. Chronoamperometric measurements were made by applying a potential of +0.45 V for 10 sec with a sampling rate of 10 Hz unless otherwise specified.

Glucose Assay Development

Three different assay approaches were evaluated including the combination of GOx and potassium ferricyanide, GDH-FAD and potassium ferricyanide, and GOx with $O_2$ and a $H_2O_2$ catalyst, Prussian Blue (PB). For the ferricyanide mediated systems, assay solutions were prepared with 1 mg/mL of the enzyme and 100 mM mediator in PBS. Assay solutions were spiked with glucose stock solutions before making chronoamperometric measurements. Briefly, PB was prepared using a previously developed protocol[23] in which a solution of 100 mM ferric chloride in 10 mM HCl was combined with 100 mM potassium ferricyanide in 10 mM HCl on the working electrode surface and allowed to set for 60 min then thoroughly washed with distilled water before using.

Absorptive Sampling Development

A soft, absorbent, eye-like surface was prepared by polymerizing a thin (1 mm) sheet of poly(2-hydroxyethyl methacrylate) (pHEMA). Briefly, pHEMA was prepared by combining the monomer, 2-hydroxyethyl methacrylate (98% purity, 200 ppm hydroquinone monomethyl ether stabilizer; HEMA), the crosslinker, ethylene glycol dimethacrylate (98% purity, 100 ppm hydroquinone monomethyl ether stabilizer; EGDMA), and thermal initiator, ammonium persulphate at ratio of 30:0.5:6 wt % in distilled water. The solution was then poured into a small container of proper dimension before heating at 60 C for 6 hr. The final sheet was washed in heated ethanol (80 C) then water (80 C) to remove any unreacted monomers or contaminants. Calcium alginate was prepared in a sheet form by pouring 1 wt % sodium alginate into a petri dish. A concentrated 2 M calcium chloride solution was gently misted onto the dish using a small atomizer, crosslinking the alginate solution. Initial screening of the materials involved testing of their ability to absorb water and then release the captured sample. This entailed placing dried, cylindrical segments of the material 0.5 mm in height and 1.0 mm in diameter in water and qualitatively evaluating the rate of absorption. Release of absorbed sample was evaluated by mechanically deforming the material and qualitatively evaluating fluid loss. For the evaluation of commercial PU foams (Studio Tools, Minneapolis), circular segments approximately 0.5 mm in height and 1.0 mm diameter were cut from larger foam squares. A small foam holder was cast in silicone rubber poly(dimethylsiloxane) (PDMS) and used to hold each segment for testing. In the experiment, a small sheet of pHEMA 5 cm by 5 cm was placed flat on a glass dish and soaked in water. Prior to sampling, the disk was tilted to pour off all excess fluid leaving a soft, hydrophillic surface with a very thin layer of water dispersed across its surface in simulation of the eye's surface. The foam segment was carefully pressed against the pHEMA for 20 sec and the change in mass was used to estimate the amount of fluid absorbed.

Results and Discussion

Quantitative Model

A model was developed based on the functional steps of tear sampling, sample dilution, and glucose detection. This model begins with the sampling of tear fluid with glucose concentration, $C_t$, into an absorbent material. This first step can be modeled as a captured fluid volume, $V_c$, with an associated standard deviation, $\sigma_c$. Next, this tear sample is extracted by an extraction solution with volume, $V_e$ ($\sigma_e$). The final result of this extraction is the dilution of the sample's glucose concentration based on the calculated dilution factor ($X_{dil}$, $\sigma_{dil}$). The dilution factor thus becomes a ratio of tear sample volume to total volume of tear sample and extraction solution (Eqn. 1). The propagation of error contributed to $X_{dilution}$ by the two variables $V_c$ and $V_e$ can be calculated by taking the square of the partial derivatives of each term multiplied by the corresponding variance term (Eqn. 2), shown in its expanded form in Eqn. 3.

$$X_{dilution}=V_c/(V_c+V_e) \tag{1}$$

$$\sigma_{dil}^2=(\delta(X_{dil})/\delta(V_c)*\sigma_c)^2+(\delta(X_{dil})/\delta(V_e)*\sigma_e)^2 \tag{2}$$

$$\sigma_{dil}^2=(-V_c/(V_c+V_e)^2*\sigma_c)^2+(V_e/(V_c+V_e)^2*\sigma_e)^2 \tag{3}$$

For simplification, the extraction efficiency is assumed to be 100%. The concentration of extracted glucose in the sensing well, $C_{glc}$, can then be calculated (Eqn. 3). Again, error propagation can be calculated in the same fashion as Eqn. 2 yielding a simplified form shown in Eqn. 5.

$$C_{glc}=X_{dil}*C_t \tag{4}$$

$$\sigma_{glc}^2=(C_t*\sigma_{dil})^2+(X_{dil}*\sigma_t)^2 \tag{5}$$

Lastly, the linear regression of the electrochemical assay must be determined and used to estimate the output current of the extracted glucose concentration. Assuming a linear relationship with slope, m, and y-intercept, b, the output current, $I_o$, can be calculated (Eqn. 6) as well as its corresponding variance (Eqn. 7) using the same approach as above.

$$I_o=m*C_{glc}+b \tag{6}$$

$$\sigma_o^2=(C_{glc}*\sigma_m)^2+(m*\sigma_{glc})^2+\sigma_b^2 \tag{7}$$

Thus, each equation in this model represents a device functionality which can be quickly tested for feasibility in an isolated experiment.

Glucose Assay Selection

The three glucose detection approaches utilized different pathways of electron flow yielding assay performance characteristics as shown in FIGS. 11A-11C. First, the combination of GOx and potassium ferricyanide was evaluated for glucose detection (FIG. 11A). While commonly used in glucose assays, at the low concentrations in tears there is a distinct lack of sensitivity (1.8 nA/μM) and poor lower limit of detection (LLD) of 500 μM. This effect could be attributed to the competitive oxidation of the enzymatic cofactor by $O_2$, resulting in decreased signal and increased variance. To address this competitive reaction, a second approach was to utilize only $O_2$ to detect the production of $H_2O_2$ during the enzymatic oxidation of glucose by GOx. By incorporating a $H_2O_2$ catalyst, PB, this product could be readily measured using low magnitude potentials. Repeating the same experiment it was found that iterative uses of a single sensor within a short time span showed an improved LLD with decreased sensitivity (0.50 nA/μM). This improved LLD is likely attributed to the undiverted flow of electrons into $H_2O_2$. FIG. 11B shows the unreplicated response of a single PB assay which pointed to a promising approach to enhanced glucose LLD.

However, it was found that PB sensors lost variable sensitivity over time in aqueous solution, a critical problem for a sensor design which requires pre-filling the well with extraction fluid. This lack of stability is noted in some literature, especially in basic solutions, and it was found that the same effect was encountered even in acidic buffers (pH 5.5).

Last, the enzyme GDH-FAD was evaluated. GDH-FAD offers the advantage of oxidizing glucose, however its FAD cofactor cannot be oxidized by $O_2$. Furthermore, unlike other forms of GDH with different cofactors, GDH-FAD does not show sensitivity to other ions in solution or cross-reactivity with other sugars as seen with the PQQ and NAD cofactors[24]. FIG. 11C shows the evaluation of the assay using 7 different disposable sensors at each concentration. A wider range of glucose concentrations were selected to highlight the improved LLD and range of the assay. An improved reproducibility and sensitivity (4.5 nA/μM) is observed over the other two approaches. This assay enjoys the simplicity and stability of GOX/Ferricyanide and the undiverted electron flow of GOX/$O_2$/PB without the drawbacks of either of the other approaches. Through further studies (data not shown) an estimated limit of detection of 2 μM was calculated.

Sampling Material Selection

One of the key functions of the proposed device is the ability to sample tears from the eye. To achieve this, an absorbent polymer featuring biocompatibility, scalability in fabrication, high absorption volume and rate, and reproducible performance would be ideal. Accordingly, three material candidates were identified: calcium alginate, pHEMA, and PU foam. The first material, calcium alginate, is a natural hydrogel created from sodium alginate, a polysaccharide obtained from sea algae which is ionically crosslinked by divalent cations such as calcium. It was found that calcium alginate in its wet state is already saturated and fails to absorb significant volumes of additional fluid. In its dry state the hydrogel matrix collapses and fails to reabsorb similar volumes again. A second material, pHEMA, showed excellent water absorption characteristics. Unfortunately, the rate of absorption was on the order of minutes rather than seconds. While rapid absorbing forms of pHEMA have been achieved by creating microporous hydrogels[25], the tradeoff in mechanical stability is undesirable. A commercial PU foam was identified which fit all of the required material characteristics and could rapidly absorb fluid into its porous structure. Pressing small cylindrical segments 1 mm in diameter and 0.5 mm in height to the simulated pHEMA eye surface, it was found that capture was rapid (<20 sec) and reproducibly on the correct volume scale (4.2±0.5 μL; n=8). Table 3 shows a summary of the evaluations of these three materials.

TABLE 3

Summary of material characteristics for calcium alginate, pHEMA, and PU foam.

| Material Requirements | Calcium Alginate | pHEMA | PU Foam |
| --- | --- | --- | --- |
| Biocompatibility | yes | yes | yes |
| Scalability | yes | yes | yes |
| High absorption ratio | no | yes | yes |
| Rapid Absorption | no | no | yes |
| Reproducibility | no | no | yes |

Model Validation

Figure 12:
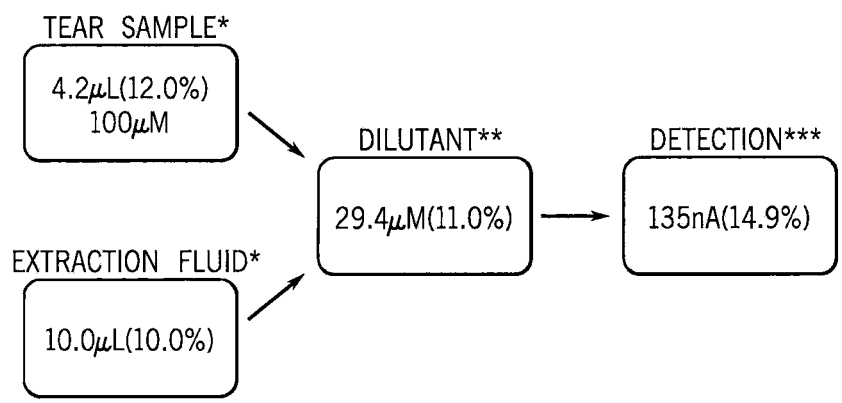
FIG. 12 shows a model of conceptual device function based on isolated experiments. Note that % RSD shown in parenthesis. Initial values (*) were obtained experimentally, or calculated using Eqns. 1 and 2-5 () or Eqns. 6-7 (*).

By isolating each key functional step of the proposed device, values and variances could be estimated for tear sampling, dilution, and glucose sensing. Input parameters for the model included terms defining how glucose would be captured and diluted ($V_c$, $V_e$, $C_t$), the response of the assay (m, b), as well as associated standard deviation for the terms. Fluid volumes and standard deviations were based on initial tests of capture and fluid injection into the devices. Based on initial sampling testing, $V_c$ was assigned a value of 4.2 μL with 12% relative standard deviation (RSD). Initial testing using a syringe pump indicated that volumes of fluid on order of 10 μL could be reproducibly dispensed with 10% RSD. The sensor response from the replicated test in FIG. 11C was used to obtain values for m (4.5 nA/μM, 10% RSD) and b (220 nA, 8.0%). It was assumed that there was no variation in $C_t$ since standard stocks were used. These values were entered into the model to estimate the system output for 100 μM glucose using Eqns 1 and 3-7 (FIG. 12).

These results indicate two important points. For the first point, it is calculated that an integrated device based on these initial results would have a dilution factor of about 2.4. With a calculated LLD for the glucose sensor of 2 μM, this would put the theoretical LLD of the proposed integrated device at about 5 μM. This LLD is an excellent level of sensitivity as many clinical studies have reported glucose concentrations ranging from 10's to 1000's of μM. However, the average volume of tear fluid on the eye is only 7 μL. Thus, it can be anticipated that a final device would need to be reduced in volume to the level of many commercial blood glucose sensors (1 μL or less of fluid).

Second, based on the model it is estimated that a 100 μM glucose tear fluid would yield 135 nA (14.9% RSD). This level of variation is promising. Currently, BG sensor variances in the United States typically range from 3% to 10% for disposable and continuous monitoring systems[26]. With a model estimated 14.9% RSD, the proposed conceptual device is promisingly close for an initial estimation. Once a prototype is constructed, it is likely that system variance could be further reduced.

EXAMPLE 3

System Integration and Model Validation of Disposable Tear Glucose Biosensor

Example 2 shows the design and testing of a new disposable tear glucose biosensor. The validation of the biosensor is further described herein. The biosensor includes an integrated fluidics portion of the prototype. The present Example shows the design, casting, and testing of the same. A sensor was created using screen printed sensors integrated with a silicone rubber fluidics system and absorbent polyurethane foam. A simulated eye surface was prepared using fluid saturated poly (2-hydroxyethyl methacrylate) sheets and the disposable prototype was tested for both reproducibility at 0, 200, and 400 μM glucose (n=7) and dynamic range of glucose detection from 0 to 1000 μM glucose.

From the replicated runs, an established RSD of 15.8% was calculated at 200 μM and a lower limit of detection was calculated at 43.4 μM. A linear dynamic range was demonstrated from 0 to 1000 μM with $R^2$ of 99.56%. The previously developed model predicted a 14.9% variation. This compares to the observed variance of 15.8% measured at 200 μM glucose.

With the newly designed fluidics component, an integrated tear glucose prototype was assembled and tested. Testing of this integrated prototype demonstrated a satisfactory lower limit of detection for measuring glucose concentration in tears and was reproducible across a physiological sampling range. The next step in the device design process will be initial animal studies to evaluate the current prototype for factors such as eye irritation, ease of use, and correlation with blood glucose.

Methods

Chemicals

All reagents were obtained from Sigma-Aldrich unless otherwise specified. Glucose dehydrogenase with flavin adenine dinucleotide cofactor (GDH-FAD) with an activity of 207 U/mg was generously donated by Amano Inc. (Japan). All solutions were prepared in phosphate buffered saline (PBS) at pH 7.4 unless otherwise specified.

Fluidics System Fabrication

For fabrication of the fluidics system, a two-part mold was created for casting. A design was made in SolidWorks (Dassault Systèmes SolidWorks Corp., Concord Ma) software and then used to fabricate the two-piece mold on a MAXNC 10 CL-EC, 3-axis CNC mill (MAX NC, Gilbert, Ariz.). The mold pieces were made from ½" thick acrylic plastic sheet (Desert Star Plastics, Phoenix, Ariz.) or aluminum T-6061 (Online Metals, Seattle, Wash.) for faster heating. For casting, a 10:1 (elastomer:curant) mixture of PDMS, Dow Corning Sylgard 184 (Ellsworth Adhesives, Germantown, Wis.) was thoroughly mixed and then degassed in a vacuum to remove air bubbles. The two-part mold was sprayed with a silicone mold release (Ease Release 200, Mann Release Technologies, Easton, Pa.) and then clamped together. The PDMS was then injected into the mold using a syringe with a 16 gauge needle and cured at 70 C for 15 min. The "soft" cured parts were then removed and were further cured at 60 C for 12 hr. For assembly, the fluidics systems were washed with a detergent (Alconox, VWR International), then water, then ethanol and then air dried. The clean fluidics systems were fixed to a screen-print sensor by applying a thin layer of uncured PDMS to the piece before carefully pressing the components together in a custom jig and heating at 60 C for 8 hr. Small segments were punched out of a sheet of absorbent commercial polyurethane foam, and one segment was carefully inserted into the sampling well of each fluidics system. Lastly, an enzymatic assay containing 1 mg/mL GDH-FAD and 100 mM potassium ferricyanide in PBS was injected into the sensing well of the device at a flow rate of 0.1 mL/hr for controlled amounts of time to dispense a fixed fluid volume and then immediately tested.

Tear Sampling Simulation

In order to evaluate the performance of the prototype, a simulation of tear fluid on the eye was created. A thin sheet of pHEMA 5 cm by 5 cm was soaked in PBS and then placed on a petri dish. Prior to sampling, the dish was tilted to pour off all excess fluid leaving a soft, hydrophillic surface with a very thin layer of fluid dispersed across its surface. This set-up roughly approximated the soft tissue of the eye with a thin distribution of tears across it. For sampling, a prepared device was pressed gently against the surface of the pHEMA to saturate the foam. The device was then set flat on the bench and the sensing well was depressed repeatedly to extract the tear sample. A chronoamperometric measurement was made immediately. The entire process from sampling to sensing took approximately 120 sec. Sheets were soaked in PBS with varying concentrations of glucose to test different concentrations. In the reproducibility study, new 7 sensors at each of the concentrations (0, 200, and 400 µM) were tested. For the dynamic range study, one new sensor was used at each concentration to measure the response from 0 to 1,000 µM glucose in 200 µM increments.

Electrochemical Detection

For electrochemical glucose sensing, a disposable, commercial screen-print sensor (Zensor, Taiwan) was selected. The sensor featured a working (71.0 mm$^2$) and counter electrode made of conductive carbon ink, a pseudoreference electrode made of silver ink (−72 mV vs Ag/AgCl), and a non-conducting insulating layer. A CHI 1230A potentiostat (CHI, Austin, Tex., USA) connected to a desktop computer was used to make electrochemical measurements. Chronoamperometric measurements were made by applying a potential of +0.45 V for 10 sec with a sampling rate of 10 Hz.

Results and Discussion

Fluidics System

Figure 13A:
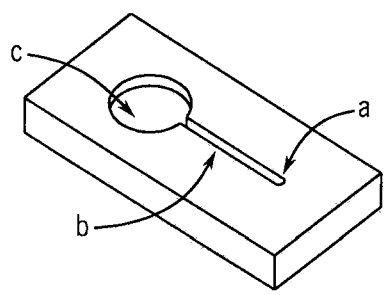
FIGS. 13A-13B show CAD schematics of the proposed fluidics portion (FIG. 13A) of the device showing underlying fluidics from sample inlet (a), channel with length, width, and height varied (b), and reservoir (c) and (FIG. 13B) interface to be in contact with the conjunctiva (d).
Figure 13B:
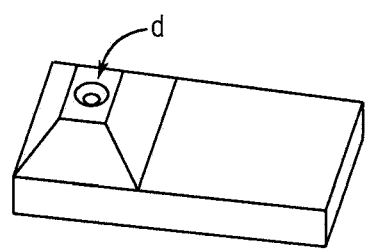

Initially, the well area also served as the sensing area, so this dimension was fixed. An initial design in CAD was made (FIGS. 13A-13B) but this was later redesigned to hold the adsorbent PU foam. Next, mold design was fabricated in acrylic in two pieces to facilitate separation and removal of the casted parts (FIGS. 14A-14B) and prototypes were cast (FIGS. 15A-15C). This initial design had a relatively large channel for fluid movement, which resulted in a 41.8 µl volume. This was found to cause an unsatisfactory dilution factor and the next design decreased both the length and width of the channel. For further iterations, sample volume was further reduced by decreasing the heights as seen in Table 4. The final fluidic device had a volume of 5.8 µl which resulted in a dilution factor of 3.5. Referring to the most recent large scale study of over 100 diabetics and non-diabetics, mean tear glucose concentrations after carbohydrate load were 0.35±0.04 mM and 0.16±0.03 respectively. A dilution factor of 3.5 puts these mean concentrations well within the sensing limits of our assay. From these prototyping results, it has become apparent that fluidic design is a primary challenge. In order to reduce variation in fluid sampling, sampling sponges must be allowed to fully saturate at a volume below the anticipated range of tear volumes on the eye. This may call for further optimization in the future to reduce dilution volumes as sample size continues to scale down.

TABLE 4

Fluidics dimensions from fabricated systems and estimated total volumes.

| Well Area (mm$^2$) | channel length (mm) | channel width (mm) | channel height (mm) | Total volume (µl) |
| --- | --- | --- | --- | --- |
| 37 | 9.4 | 1.9 | 0.76 | 41.8 |
| 37 | 5.6 | 1.5 | 0.76 | 34.6 |
| 37 | 5.6 | 1.5 | 0.51 | 23.1 |
| 37 | 5.6 | 1.5 | 0.25 | 11.5 |
| 37 | 5.6 | 1.5 | 0.13 | 5.8 |

Electrochemical Detection

Figure 16:
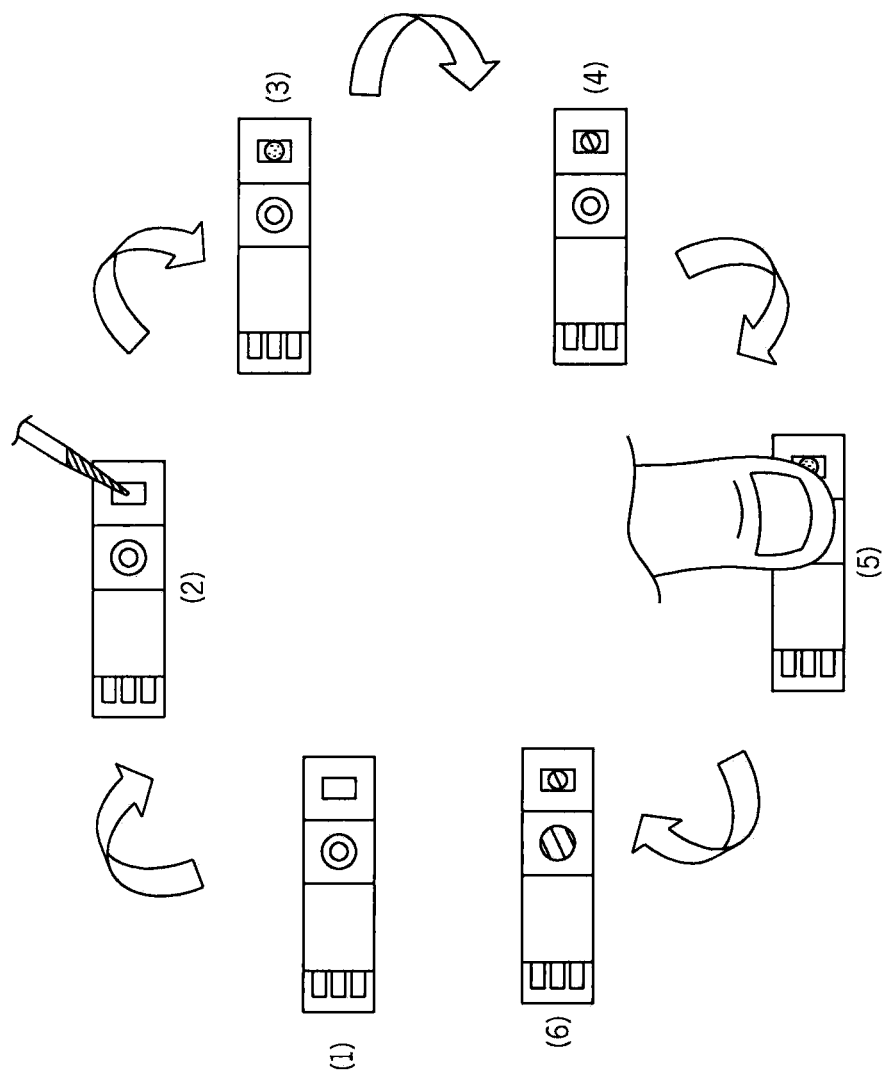
FIG. 16 shows a schematic of operation showing (1) A sensor is prepared, the sample is pipetted (2) into the foam capture material (3), under 365 nm (UV) stimulation the dye can be visualized (4), when pressure is applied to the sensing region (5) and released (6) under UV stimulation, the dye can be seen to flow down the channel and into the sensing region itself.

Operation of the device once assembled is simple (FIG. 16). Simply touching the device to a moist surface allows for the adsorbent layer to absorb a fixed volume of fluid. Then, by applying and removing slight pressure onto the reservoir-pump region, mixing of reagents and the sample occurs and the sensor is ready for detection. In the figure, UV light shows the clean dispersal of the "sample", here a fluorescent dye, rhodamine 6G. The simple functionality of this device is critical for a successful design. Approaches to tear glucose measurement have been hampered by the challenge of integrating a sensitive sensing technology with an easy approach to sampling.

Figure 17A:
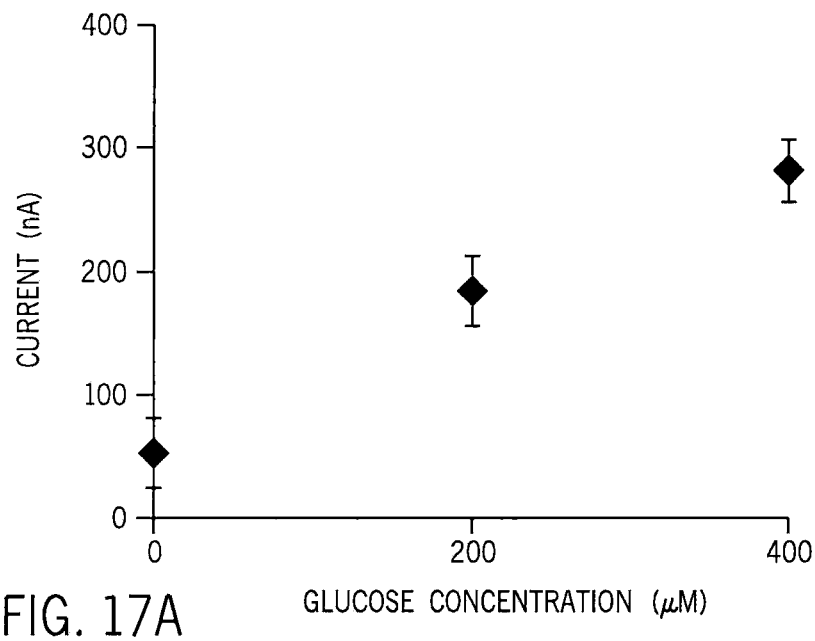
FIG. 17A shows experimental results demonstrating reproducibility of sampler-electrodes at 0, 200 and 400 µM glucose concentration (n=7).
Figure 17B:
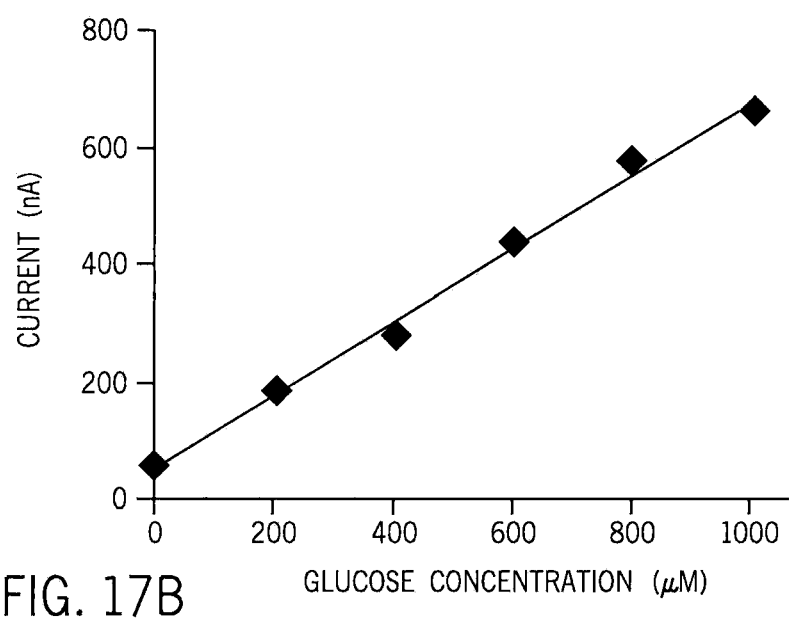
FIG. 17B. Experimental results demonstrating dynamic range with 0 to 1,000 µM of glucose in steps of 200 µM with line representing a linear regression of the data with $R^2$ of 0.9956.

A reproducibility (n=7) study (FIG. 17A) was performed at concentrations of 0, 200, and 400 µM glucose in the fully integrated system. Current levels were recorded over time and the current at 9.9 sec was recorded (time to reach ~95% response time) and plotted against the concentration. An RSD of 15.8% was measured at near physiological levels of TG (200 μM) using seven separate devices. Comparing these results with the error estimation model developed in Part 1 of this work, the estimated RSD for the system was 14.9%, supporting the accuracy of the model. A test was performed over the dynamic range of 0 to 1,000 μM in increments of 200 μM (FIG. 17B). A linear regression was calculated with an $R^2$ of 99.56%. This result demonstrates that the device is capable of glucose within the concentration range reported by the majority of previous tear glucose research. Next, the baseline (0 μM) standard deviation was later used to calculate limits of detection. From this data and the previous estimates of the baseline standard deviation (×3), a LLD of 43.4 μM was calculated. This result is eight times higher than expected. Comparing the linear regression in from our previous work with this result, there is a 7.2 times decrease in response slope for the new data. This accounts for the majority of the error in the estimation of LLD. One possible reason for this decrease in sensitivity is non-ideal sample extraction. Also, the slight increase in RSD can likely be attributed to the several steps in sensor assembly which require manual assembly and may introduce variation unaccounted for in the model.

Conclusion

The device of the present invention tested in the Examples herein is capable of detecting physiological glucose concentrations within the ranges commonly presented in literature. Namely, linearity over the range of 0 to 1,000 μM (R2 of 0.9956) and 15.8% RSD reproducibility of the device has been demonstrated. Assessment of device variability matches predicted models presented previously. Further the disposable prototype is readily manufactured in modest quantities using standard fabrication technologies.

The invention claimed is:

1. A device for determining the presence of an analyte in a fluid sample comprising:
   a. a collection chamber containing an absorbent hydrogel material configured to absorb an analyte;
   b. a fluidic channel connected to the collection chamber;
   c. a sensing chamber connected to the fluidic channel;
   d. a compressible housing configured to facilitate transfer of an extraction fluid contained in the sensing chamber to the collection chamber upon compression of said housing, the extraction fluid capable of dissolving the absorbed analyte, the compressible housing further configured to provide transfer of the analyte laden extraction fluid back to the sensing chamber upon release of said housing,
   wherein a material that specifically detects the analyte is contained in the fluidic channel or the sensing chamber, and
   wherein the sensing chamber is operably linked to a processor containing a potentiostat that allows detection of the analyte using electrochemical sensing.

2. The device of claim 1 wherein the processor containing a potentiostat is an electrode system wherein the processing of the fluid comprises applying a voltage to the electrode system to induce an electrochemical reaction between the material that specifically detects the analyte and the analyte in the fluid sample and detecting a current produced by the electrochemical reaction from the contact of the analyte with the material that specifically detects the analyte.

3. A method of determining the concentration of an analyte in a fluid sample comprising:
   a. providing the device of claim 1;
   b. receiving said fluid into the collection chamber of said device;
   c. transferring the liquid collected in step (b) to the sensing chamber of said device by compressing and releasing the compressible housing of said device to determine the presence of said analyte in said fluid; and
   d. correlating the determined presence of the analyte in said liquid with a concentration of said analyte in said liquid.

4. The method of claim 3 wherein said analyte is glucose.

5. The method of claim 3 wherein said fluid sample is tear fluid.

6. The method of claim 3 wherein said receiving said fluid in the collection chamber comprises placing a tip of the collection chamber well near the eye region of a subject.

7. The method of claim 5 wherein the tear fluid sample is between about 1 μl to about 10 μl.

8. The method of claim 4, wherein the material that specifically detects the analyte comprises glucose oxidase or glucose dehydrogenase.

9. The method of claim 8, wherein the glucose oxidase or glucose dehydrogenase comprises dry reagents contained within the fluidic channel for mixing with the extraction fluid upon transfer of the extraction fluid from the sensing chamber to the collection chamber.

10. The method of claim 9 wherein the device detects physiological glucose concentrations at a linear rate over a concentration range of 0 μM to 1,000 μM.

11. The device of claim 1, wherein a volume of the extraction fluid contained in the sensing chamber is substantially a constant volume.

12. The device of claim 1, wherein the hydrogel material is configured to absorb at least 10 percent by weight of water.

13. The device of claim 1, wherein a volume of the analyte absorbed by the absorbent hydrogel material comprises substantially a known amount of analyte.

14. The device of claim 1, wherein the extraction fluid contained in the sensing chamber comprises the material that specifically detects the analyte and the material that specifically detects the analyte comprises glucose oxidase or glucose dehydrogenase.

15. The device of claim 1, wherein the analyte comprises an analyte in a tear fluid sample exhibiting a volume between about 1 μl to about 10 μl.

16. The device of claim 1, wherein the material that specifically detects the analyte is contained in the fluidic channel and comprises dry reagents.

17. The device of claim 1, wherein the material that specifically detects the analyte comprises dry reagents including at least one of glucose oxidase or glucose dehydrogenase, the dry reagents contained within the fluidic channel for mixing with the extraction fluid upon transfer of the extraction fluid from the sensing chamber to the collection chamber.

18. The device of claim 1, wherein the absorbent hydrogel material comprises a polyurethane foam.

* * * * *